United States Patent
Oak et al.

(10) Patent No.: US 11,432,798 B2
(45) Date of Patent: Sep. 6, 2022

(54) PORTABLE PROBE FOR PHOTOACOUSTIC TOMOGRAPHY AND REAL-TIME PHOTO ACOUSTIC TOMOGRAPHY DEVICE

(71) Applicant: PUKYONG NATIONAL UNIVERSITY INDUSTRY-UNIVERSITY COOPERATION FOUNDATION, Busan (KR)

(72) Inventors: Chul Ho Oak, Busan (KR); Eun Kee Park, Busan (KR); Jung-Eun Park, Busan (KR); Yeh Chan Ahn, Busan (KR)

(73) Assignee: PUKYONG NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 117 days.

(21) Appl. No.: 17/013,664

(22) Filed: Sep. 7, 2020

(65) Prior Publication Data
US 2020/0397404 A1 Dec. 24, 2020

Related U.S. Application Data

(63) Continuation of application No. 16/464,701, filed as application No. PCT/KR2017/011720 on Oct. 23, 2017, now abandoned.

(30) Foreign Application Priority Data

Nov. 30, 2016 (KR) ........................ 10-2016-0161637

(51) Int. Cl.
*A61B 8/13* (2006.01)
*A61B 5/00* (2006.01)
(Continued)

(52) U.S. Cl.
CPC .............. *A61B 8/13* (2013.01); *A61B 5/0033* (2013.01); *A61B 5/0062* (2013.01);
(Continued)

(58) Field of Classification Search
CPC ........ G01N 29/24; A61B 8/13; A61B 8/4444; A61B 8/483; A61B 5/0033; A61B 5/0062; A61B 5/0073
(Continued)

(56) References Cited

U.S. PATENT DOCUMENTS 5,055,653 A * 10/1991 Funami .............. B23K 26/0643
219/121.75
2005/0170572 A1* 8/2005 Hongo ................ B23K 26/0738
250/341.1
(Continued)

FOREIGN PATENT DOCUMENTS

CN 102324686 A * 1/2012
JP 2011229609 A * 11/2011 ........... A61B 5/0073
(Continued)

OTHER PUBLICATIONS

Machine Translation of JP-2011229609-A (Year: 2011).*
(Continued)

*Primary Examiner* — Amelie R Davis
*Assistant Examiner* — John Denny Li
(74) *Attorney, Agent, or Firm* — Patent Office of Dr. Chung Park (57) ABSTRACT

The present invention relates to a portable probe for photoacoustic tomography, capable of performing line-by-line scanning or area-by-area scanning by using a small number of light inputs; and a real-time photoacoustic tomography device. The probe for photoacoustic tomography includes: a lens receiving light inputs from an optical fiber so as to make the same proceed as small diameter parallel light; a Powell
(Continued)

lens receiving the small diameter parallel light and generating a line beam of a predetermined thickness, and allowing energy dispersed on a line to be uniform on the entire line; a lens making the line beam pass therethrough such that the line beam has a predetermined width and a reduced thickness so as to be line-focused at a target area; an acoustic reflection glass for separating, from a light path, an acoustic wave outputted from the target area; and an acoustic measurement unit for measuring acoustic strength.

6 Claims, 7 Drawing Sheets

(51) Int. Cl.
    *A61B 8/00*         (2006.01)
    *G01N 29/24*      (2006.01)
    *A61B 8/08*         (2006.01)

(52) U.S. Cl.
    CPC .......... *A61B 5/0073* (2013.01); *A61B 8/4444* (2013.01); *G01N 29/24* (2013.01); *A61B 8/483* (2013.01)

(58) Field of Classification Search
    USPC ......................................................... 600/459
    See application file for complete search history.

(56) References Cited

U.S. PATENT DOCUMENTS

| | | | | |
|---|---|---|---|---|
| 2015/0069267 | A1* | 3/2015 | Feng | ................. G02B 21/0032 |
| | | | | 250/459.1 |
| 2016/0103310 | A1* | 4/2016 | Tomaselli | .......... G02B 21/0032 |
| | | | | 359/385 |
| 2017/0179675 | A1* | 6/2017 | Clark | ................ G02B 27/0927 |

FOREIGN PATENT DOCUMENTS

| | | | |
|---|---|---|---|
| JP | 2013027482 A | * | 2/2013 |
| KR | 20140122988 A | * | 10/2014 |

OTHER PUBLICATIONS

Machine Translation of JP-2013027482-A (Year: 2013).*
Machine Translation of KR20140122988A (Year: 2014).*
Machine Translation of CN102324686A (Year: 2011).*

\* cited by examiner

PORTABLE PROBE FOR PHOTOACOUSTIC TOMOGRAPHY AND REAL-TIME PHOTO ACOUSTIC TOMOGRAPHY DEVICE

TECHNICAL FIELD

The present invention relates to a portable probe for photoacoustic tomography and a real-time photoacoustic tomography device, and more particularly, to a portable probe for photoacoustic tomography, which can produce an image of an internal biological tissue of an object in vivo using a photoacoustic effect, and a real-time photoacoustic tomography device.

BACKGROUND ART

A photoacoustic tomography device images an internal biological tissue of an object in vivo using photoacoustic imaging. The photoacoustic imaging enables biological tissues to be imaged in vivo (noninvasively) using a photoacoustic effect. The photoacoustic effect refers to an effect in which an acoustic wave is generated when an absorptive material (in vivo or ex vivo) absorbs light or an electromagnetic wave, such as a radio wave.

Here, if short electromagnetic pulses of laser are incident to a biological tissue, some of the energy is absorbed into the absorptive material of the tissue to then be converted into heat, causing thermo-elastic expansion. As a result, an ultrasonic wave having a broadband frequency is emitted, and the emitted ultrasonic wave is measured in many directions using an ultrasonic transducer to convert the same into an image.

The photoacoustic tomography device is combined medical imaging equipment including an ultrasonic imaging device and optical equipment, which can offset the respective disadvantages of the ultrasonic imaging device and the optical equipment. That is to say, the photoacoustic tomography device is hybrid equipment combining optical equipment with an ultrasonic imaging device to compensate for a low image contrast, which is a disadvantage of the ultrasonic imaging device, and a short transmission depth, which is a disadvantage of the optical equipment, thereby providing a higher image contrast than the ultrasonic imaging device and a deeper transmission image than the optical equipment.

In conventional confocal photoacoustic tomography devices, however, beams are collected at a point to be irradiated into a scanning spot and an ultrasonic wave outputted from the point is acquired. Therefore, in order to obtain a three-dimensional image, scanning is performed by moving a light source or using an array of multiple light sources.

Technical Problems to be Solved

The present invention has been made in an effort to solve the problems of the prior art, and it is an object of the present invention to provide a portable probe for photoacoustic tomography, capable of performing line-by-line scanning or area-by-area scanning by using a small number of light inputs, and a real-time photoacoustic tomography device. In addition, the present invention provides a photoacoustic tomography device without a concentration measurement distortion of an absorptive material due to a non-uniform beam energy distribution in an imaging area, by converting line beams emitted from a light source having a non-uniform energy distribution, into line beams having a uniform energy distribution with a Gaussian distribution.

Technical Solutions

In accordance with an aspect of the present invention, the above and other objects can be accomplished by providing a probe for photoacoustic tomography, the probe including a lens receiving light inputs from an optical fiber so as to make the same proceed as small diameter parallel light, a Powell lens receiving the small diameter parallel light so as to generate a line beam with uniform energy distribution, a lens making the line beam pass therethrough such that the line beam has a predetermined width and a reduced thickness so as to be line-focused at a target area, an acoustic reflection glass for separating, from a light path, an acoustic wave outputted from the target area, and an acoustic measurement unit receiving an acoustic wave outputted from the target area.

The lens may include a collimator receiving the light inputs so as to generate parallel light having a predetermined diameter.

The lens may include a condenser lens making the line beam pass therethrough such that the line beam has a uniform energy distribution, a predetermined width and a reduced thickness so as to be line-focused at the target area.

The Powell lens may include a pair of Powell lenses spaced a predetermined distance apart from each other and receiving light inputs as parallel light beams so as to generate line beams, respectively, and the lens may include a first cylinder lens allowing the respective line beams to pass therethrough so as to generate the respective parallel light beams having a predetermined width and a predetermined thickness, and a second cylinder lens allowing the respective parallel light beams to pass therethrough so as to be line-focused at the target area as a single line beam.

The first cylinder lens and the second cylinder lens may be arranged such that convex portions thereof are rotated at 90 degrees with respect to the central axis of the beam traveling direction and face each other.

The acoustic measurement unit may be placed on a line bisecting a space between the respective parallel light beams on center lines of the parallel light beams to provide a dark field illumination structure.

The probe may further include a reflection plane located at a side of the target area to allow the acoustic wave outputted from the target area to be incident to the acoustic measurement unit by allowing the incident light to pass therethrough and changing a traveling path of the acoustic wave.

The lens may include a variable focus lens and mechanism capable of controlling a focusing depth within a tissue, on which the line beam is focused, at the target area.

In accordance with another aspect of the present invention, the above and other objects can be accomplished by providing a probe for photoacoustic tomography, the probe including a Powell lens receiving a light input from a collimator as small diameter parallel light so as to generate a line beam having a uniform energy distribution, a lens allowing the line beam to pass therethrough so as to generate parallel light having a predetermined width and a predetermined thickness, a light path changing unit along the parallel light to pass therethrough so as to be area-focused at a target area, and an acoustic measurement unit receiving an acoustic wave outputted from the target area.

The lens may include a cylinder lens having a convex portion positioned at a light emitting side.

The light path changing unit may include a beam splitter member splitting one single parallel light beam into a first parallel light beam and a second parallel light beam, and a pair of light path changing members changing light paths of the first parallel light beam and the second parallel light beam so as to be area-focused at the target area.

The beam splitter member may include a pair of prisms having acute angle portions adjoining each other.

Each of the light path changing members may include a pair of prisms having right-angled faces facing each other.

The acoustic measurement unit may be positioned between the pair of light path changing members.

The beam splitter member may include a pair of prisms having acute angle portions adjoining each other, each of the light path changing members may include a pair of prisms having right-angled faces facing each other, and focusing positions may be controlled by adjusting positions or angles of at least one of the prisms included in the beam splitter member and the light path changing members.

In accordance with still another aspect of the present invention, the above and other objects can be accomplished by providing a probe for photoacoustic tomography, the probe including a pair of Powell lenses spaced a predetermined distance apart from each other and receiving light inputs as parallel light beams so as to generate line beams, respectively; a cylinder lens allowing the respective line beams to pass therethrough so as to generate the respective parallel light beams having a predetermined width and a predetermined thickness; a pair of light path changing members changing light paths of the parallel light beams to then be area-focused at the target area; and an acoustic measurement unit receiving an acoustic wave outputted from the target area.

The acoustic measurement unit may be positioned between the pair of light path changing members.

The pair of light path changing members may be spaced apart from each other and include a pair of prisms having right-angled faces facing each other.

Focusing positions may be controlled by adjusting positions or angles of the prisms.

In accordance with still another aspect of the present invention, the above and other objects can be accomplished by providing a probe for photoacoustic tomography, the probe including a Powell lens receiving a light input from a collimator as the small diameter parallel light so as to generate a line beam having a uniform energy distribution, and allowing energy distributed on a line to be uniform on the entire line, at least one lens irradiating the line beam so as to be line-focused or area-focused at a target area, and an acoustic measurement unit receiving an acoustic wave outputted from the target area.

The acoustic measurement unit may be located so as not to be interfered with the laser beam focused into the target area.

The acoustic measurement unit may include an array of a plurality of linear ultrasonic transducers arranged linearly.

In accordance with still another aspect of the present invention, the above and other objects can be accomplished by providing a photoacoustic tomography device including the probe for photoacoustic tomography.

Advantageous Effects

As described above, according to the present invention, line-by-line scanning or area-by-area scanning can be performed by using a small number of light inputs, thereby quickly acquiring an image for a wide area using a simple device. In addition, the energy can be uniformly distributed into an area for line or area scanning, thereby acquiring a uniform image in an imaging area.

BRIEF DESCRIPTION OF DRAWINGS

For a better understanding of the present disclosure, preferred embodiments thereof are now described, purely by way of non-limiting example and with reference to the attached drawings, wherein.

BEST MODE FOR CARRYING OUT THE INVENTION

Hereinafter, a preferred embodiment of the present invention will be described in detail. In the following description, the present invention will be explained by way of example with regard to a probe for photoacoustic tomography and a real-time photoacoustic tomography device shown in the drawings, but the invention is not limited to the shown probe and device. In the following embodiments, like numbers refer to like elements throughout, and cross reference will be made to descriptions of those elements.

Figure 1:
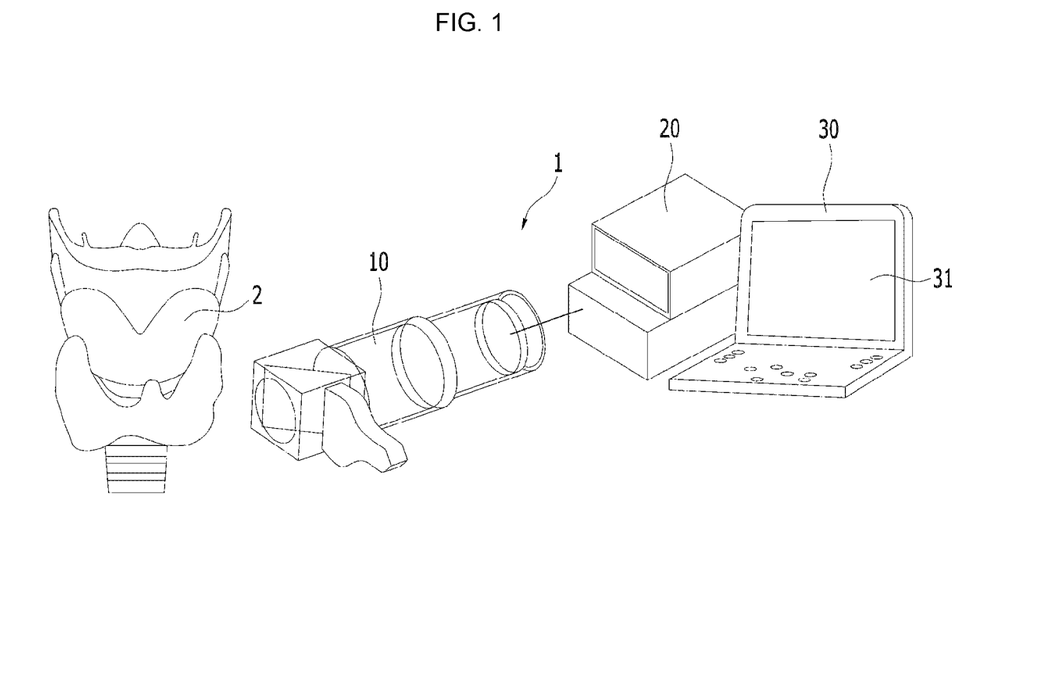
FIG. 1 is a schematic diagram of a real-time photoacoustic tomography device according to an embodiment of the present invention.
Figure 2:
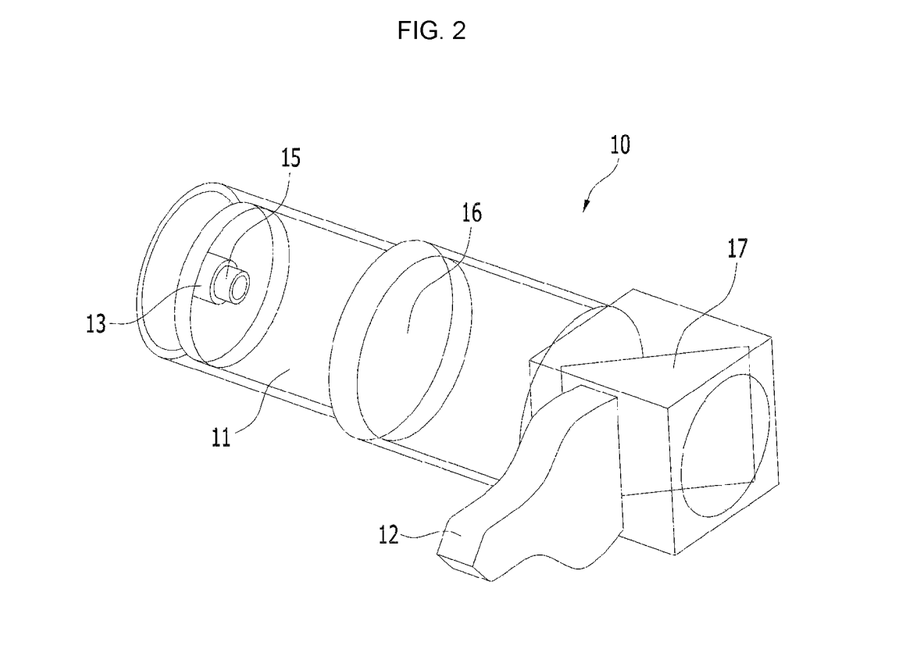
FIG. 2 is a schematic diagram of a probe for photoacoustic tomography according to an embodiment of the present invention.
Figure 7:
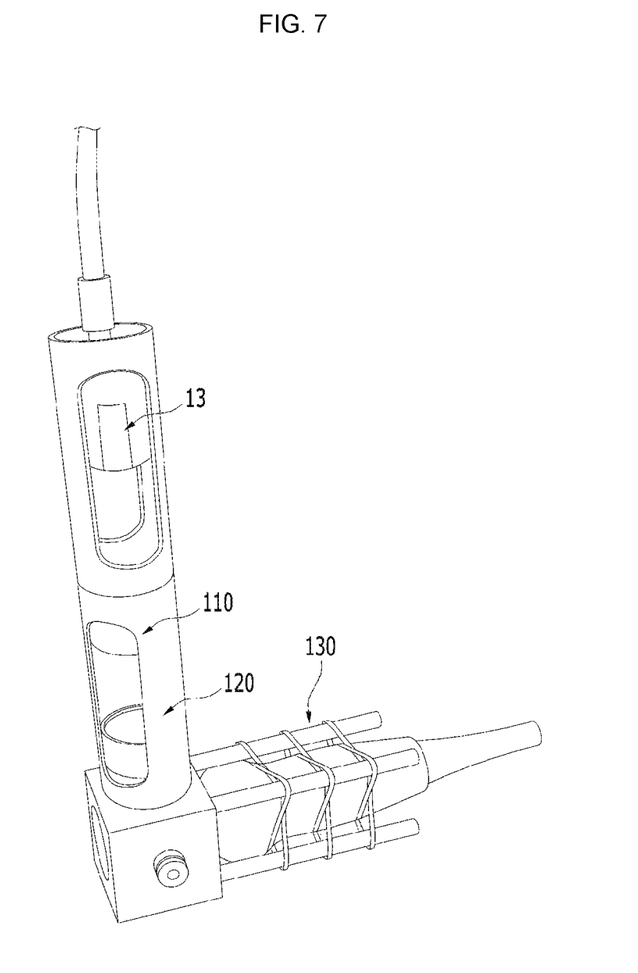
FIG. 7 shows an actual implementation example of the probe for photoacoustic tomography according to an embodiment of the present invention.
Figure 8:
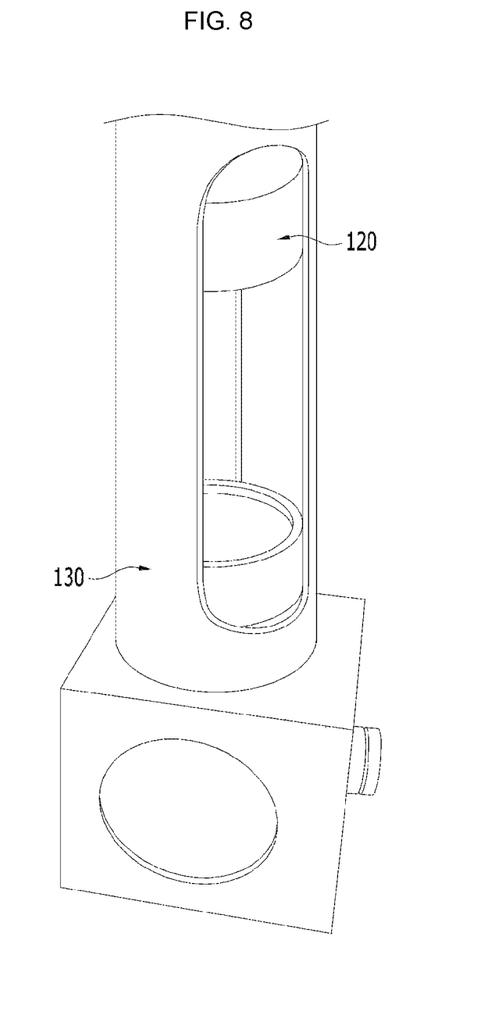
FIG. 8 shows an example of line focusing observed through the actual implementation example of the probe for photoacoustic tomography according to an embodiment of the present invention.

FIG. 1 shows a real-time photoacoustic tomography device 1 according to an embodiment of the present invention. FIG. 2 shows a probe 10 for photoacoustic tomography according to an embodiment of the present invention. FIGS. 7 and 8 show actual implementation examples of the probe 10 for photoacoustic tomography according to an embodiment of the present invention.

Referring to FIG. 1, the photoacoustic tomography device 1 may include a photoacoustic probe 10, a laser generation unit 20, and a photoacoustic control unit 30.

The photoacoustic probe 10 irradiates laser beams inputted from the laser generation unit 20 into a target object 2 and receives an acoustic wave outputted from the target object 2 to then output the acoustic wave to the photoacoustic control unit 30. The photoacoustic probe 10 may be implemented through an optical design having one of internal constructions shown in FIGS. 3 to 6.

The laser generation unit 20 may generate short-wavelength laser, multi-wavelength laser, or tunable pulse laser.

The laser generation unit 20 may include a variety of laser sources, including a semiconductor laser diode (LD) generating a particular wavelength component or monochromatic light including the particular wavelength component, a light emitting diode (LED), solid laser, or gas laser. Here, laser generation unit 20 may include a plurality of laser sources having different wavelengths.

The laser generation unit 20 may generate a laser beam of a wavelength corresponding to the target object 2. To this end, the laser generation unit 20 may be connected to the photoacoustic control unit 30 to receive a user input through the photoacoustic control unit 30 and may synchronize a time of outputting the laser beam with an acoustic measurement time. Alternatively, the laser generation unit 20 may receive a user input through the laser generation unit 20 and may synchronize an acoustic measurement time with a time of outputting the laser beam.

The photoacoustic control unit 30 may receive a photoacoustic signal collected through the photoacoustic probe 10 to then convert the photoacoustic signal into a photoacoustic image. The photoacoustic control unit 30 may include a display unit 31 to display the photoacoustic image converted from the photoacoustic signal. In addition, the display unit 31 may display various kinds of information including the operation and progress of a device associated with generation of the photoacoustic image, and details relevant to the user input.

In addition, the photoacoustic control unit 30 may include various types of user input units receiving user inputs. Here, user input details inputted through the user inputs may be displayed on the display unit 31.

Meanwhile, the laser generation unit 20 may include a laser source, an attenuator, and connection terminals. The laser source may generate laser beams having various wavelengths corresponding to a target object. The attenuator may attenuate the strength of a laser beam generated from the laser source so as to be suitable for photoacoustic tomography. An optical fiber may be connected through the connection terminals and then connected to the photoacoustic probe through a collimator for producing a flux of parallel light beams from the optical fiber.

Here, if short electromagnetic pulses of laser are incident to a biological tissue that is a target object, some of the energy is absorbed into an absorptive material of the tissue to then be converted into heat, causing thermo-elastic expansion. As a result, an ultrasonic wave having a broadband frequency is emitted, and the emitted ultrasonic wave is measured using an acoustic measurement unit, such as an ultrasonic transducer. The measured signal is transmitted to a photoacoustic control unit to then be produced as an image of the biological tissue as the target object.

In a general optical imaging device, wavelengths of laser may be increased for the purpose of increasing a penetration depth. In this case, the degree of resolution may be undesirably lowered. In the photoacoustic tomography device 1 according to the present invention, however, since an ultrasonic signal is measured after irradiating light beams, the penetration depth can be increased without lowering the resolution.

The laser generation unit 20 generates laser beams having a wavelength range suited to an absorption coefficient of an absorptive material of the target object and then irradiates the generated laser beams into a target area to obtain a photoacoustic image of the target object. Here, in order to obtain photoacoustic images for a plurality of target objects, laser beams having a plurality of wavelength ranges corresponding thereto may be sequentially irradiated. In such a manner, the photoacoustic images for the respective target objects can be obtained altogether.

The photoacoustic probe 10 may include a main body 11, an acoustic measurement unit 12, and an optical fiber connection unit 13. The main body 11 includes an internal construction and arrangement based on an optical design for converting a light beam radiated from an optical fiber using a collimator into small diameter parallel light to generate a line beam and then performing line focusing or area focusing on a target area according to the present invention. Specific embodiments of the construction and arrangement based on the optical design are shown in FIGS. 3 to 6. Therefore, the photoacoustic tomography device may have all of technical features and effects of the photoacoustic probe 10 shown in FIGS. 3 to 6.

The main body 11 is connected to an optical fiber through the optical fiber connection unit 13 to transmit the laser beam generated from the laser generation unit 20. The main body 11 converts the laser beam generated from the laser generation unit 20 into parallel light through the optical fiber and the optical fiber connection unit 13 to allow the parallel light to be line-focused or area-focused at the target area. The collimator is positioned at an end of the optical fiber in the optical fiber connection unit 13 to make the laser beam radiated from the optical fiber proceed as parallel light so as not to be radiated unlimitedly, but aspects of the present invention are not limited thereto. Rather, a variety of members capable of performing such functions can be used.

The acoustic measurement unit 12 measures an acoustic wave generated by the laser beam irradiated into the target area, and an ultrasonic transducer may be used as the acoustic measurement unit 12. Here, the acoustic measurement unit 12 may be an array of a plurality of linear ultrasonic transducers arranged linearly so as to effectively measure the acoustic wave outputted from the line-focused or area-focused laser beam. That is to say, since the acoustic measurement unit 12 may linearly receive acoustic waves outputted line by line or area by area through the linear ultrasonic transducer array, an image for a wide area can be quickly acquired.

According to the present invention, line-by-line scanning or area-by-area scanning can be performed by using a small number of light inputs, thereby quickly acquiring an image for a wide area using a simple device.

To this end, the photoacoustic probe 10 may include a collimator 13, a Powell lens 15, a lens 16, and an acoustic measurement unit 12.

The collimator 13 converts the laser beam radiated from the optical fiber into a flux of parallel light beams having a constant diameter so as to make the laser beam proceed as parallel light. The Powell lens 15 receives small diameter parallel light as an optical input so as to generate a line beam of a predetermined thickness. The lens 16 may irradiate the line beam so as to be line-focused or area-focused at the target area. The acoustic measurement unit 12 may receive the acoustic wave outputted by irradiating the line beam from the target area.

The collimator 13, which converts the laser beam radiated from the optical fiber into a parallel light beam flux, may prevent the laser beam from being radiated unlimitedly and may allow beams entering the Powell lens 15 to have a constant size, thereby maintaining the optical design.

The Powell lens 15 may receive the small diameter parallel light so as to generate a line beam of a predetermined thickness and uniform strength. In this case, the line beam may be line-focused on a surface perpendicular to a beam traveling direction with substantially uniform strength.

That is to say, the photoacoustic probe 10 employs an optical design using the Powell lens 15, thereby irradiating light into an imaging area with uniform energy strength. Therefore, the photoacoustic probe 10 enables quantitative image acquisition without a concentration measurement distortion of an absorptive material, thereby accurately obtaining a precise image for the target area.

The lens 16 is provided for allowing the line beam to be line-focused or area-focused at the target area and may include at least one lens having a variety of shapes, constructions and arrangements. Here, the lens is a member for changing a light path of incident light, and a single member or a combination of a plurality of members having a variety of shapes may be used as the lens.

Meanwhile, the photoacoustic probe 10 may be configured so as to control a depth of the line beam focused at the target area in the biological tissue. Therefore, the focusing depth or size of the target area can be freely controlled, and a photoacoustic image for the target area can be easily obtained while minimizing movement of the photoacoustic probe 10.

In order to implement a structure capable of controlling the focusing depth in the tissue, various embodiments of the structure can be effected. In an embodiment, the focusing depth may be controlled by changing positions of the lens 16 while moving the lens 16 forward or backward along the light path. In another embodiment, a variable focus lens may be used as the lens 16. In this case, the tissue focusing depth controlling structure can be easily implemented using a general focus controlling mechanism, including, for example, a liquid lens capable of controlling refractive power of lens.

In still another embodiment, the tissue focusing depth controlling structure can be implemented by adjusting positions or angles of prisms used to change a light path.

Here, the focusing depth controlling structure may be connected to the photoacoustic control unit 30 to then be controlled by the photoacoustic control unit 30. A user input may be received through the photoacoustic control unit 30 and the focusing depth within the tissue may be controlled by the user input.

Meanwhile, the acoustic measurement unit 12 is preferably located so as not to be interfered with the laser beam irradiated into the target area. To this end, the acoustic measurement unit 12 may be positioned at 90 degrees or 180 degrees with respect to the light path of the laser beam irradiated into the target area. In this case, a reflection plane 17 may be located at an end of the target area of the photoacoustic probe 10 based on a property of the acoustic wave propagating only in a medium, for example, water. The reflection plane 17 allows the acoustic wave to be incident to the acoustic measurement unit 12 by separating the acoustic wave from the light path to change a traveling path of the acoustic wave such that the incident light is allowed to pass therethrough and only the acoustic wave outputted from the reflection plane 17 is reflected.

Figure 3:
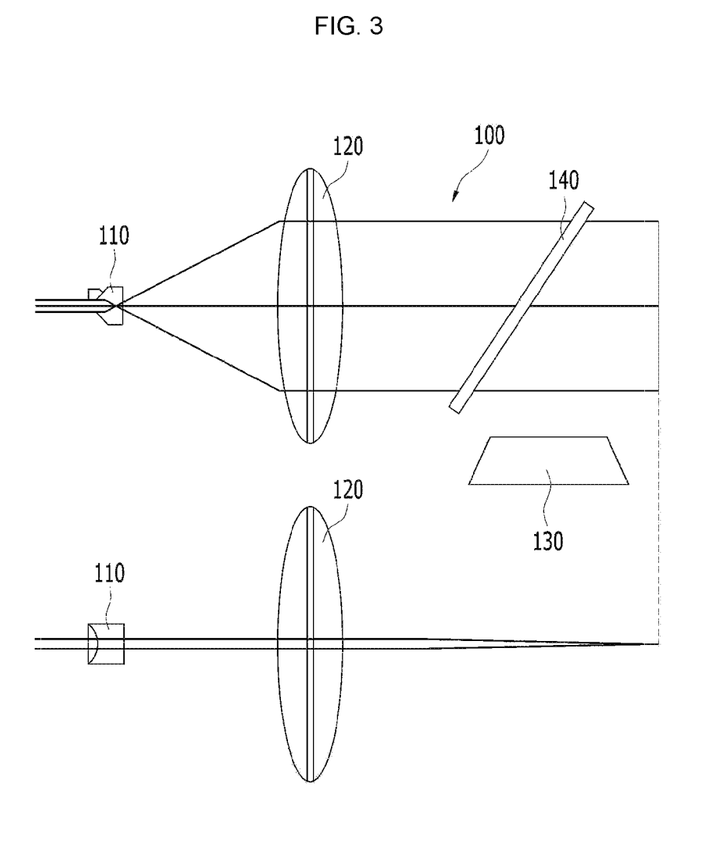
FIG. 3 is a schematic diagram illustrating an internal construction of a probe for photoacoustic tomography according to another embodiment of the present invention.

FIG. 3 illustrates a first embodiment of an internal construction of a probe 100 for photoacoustic tomography according to the present invention. In the illustrated embodiment, small diameter parallel light generated by a collimator in an optical fiber input unit is converted into a line beam and then line-focused at a target area. Here, a plan view of an optical system is shown in the upper part of FIG. 3, and a side view of the optical system rotated at 90 degrees with respect to the plan view is shown in the lower part of FIG. 3.

Referring to FIG. 3, the photoacoustic probe 100 may include a Powell lens 110, a condenser lens 120, and an acoustic measurement unit 130.

The Powell lens 110 may receive parallel light from the collimator so as to generate a line beam of a predetermined thickness. The condenser lens 120 allows the line beam to pass therethrough such that the line beam has a predetermined width and a reduced thickness in a beam traveling direction so as to be line-focused at a target area. The acoustic measurement unit 130 may receive an acoustic wave outputted from the target area.

When the Powell lens 110 receives parallel light from the collimator so as to generate a line beam of a predetermined thickness, the line beam, which has a predetermined thickness and a width increased a predetermined angle with respect to the center line of a plane, may be incident to a surface perpendicular to the beam traveling direction with substantially uniform strength.

The photoacoustic probe 100 may employ an optical design using the Powell lens, thereby irradiating light into an imaging area with uniform energy strength, thereby acquiring an image from the target area without a concentration measurement distortion of an absorptive material. Therefore, the photoacoustic probe 100 enables quantitative image acquisition, thereby accurately obtaining a precise image for the target area.

The beam generated from the condenser lens 120 may have a constant width on a plane and a thickness reduced at a predetermined rate in the beam traveling direction and may be line-focused at the target area for photoacoustic tomography.

Here, the condenser lens 120 may control a focusing depth within a tissue by changing its positions while moving forward or backward along the light path. In addition, the condenser lens 120 may include a variable focus lens. In this case, the focusing depth controlling structure can be easily implemented using a general focus controlling mechanism.

Here, the photoacoustic probe 100 is configured such that the focusing depth within the tissue, on which the line beam is focused, can be controlled, thereby freely controlling focusing depths or sizes of the target area. Accordingly, photoacoustic images for the respective depths of the target area can be easily obtained while minimizing movement of the photoacoustic probe 100.

As such, a three-dimensional image for the target area can be obtained by performing line scanning while minimizing movement of the photoacoustic probe 100.

Meanwhile, the acoustic measurement unit 130 may include an ultrasonic transducer receiving an acoustic wave outputted from the target area. Here, the acoustic measurement unit 130 may be an array of a plurality of linear ultrasonic transducers arranged linearly so as to effectively measure the acoustic wave outputted from the line-focused or area-focused laser beam. That is to say, since the acoustic measurement unit 130 may linearly receive acoustic waves outputted line by line or area by area through the linear ultrasonic transducer array, an image for a wide area can be quickly acquired. Accordingly, the real-time photoacoustic tomography device can be easily implemented.

A reflection plane 140 may be located at a side of the target area and may allow the acoustic wave to be incident to the acoustic measurement unit 130 by allowing incident parallel light to pass therethrough and changing a traveling path of the acoustic wave outputted therefrom. In this case, the acoustic measurement unit 130 is located so as not to be interfered with the laser beam irradiated into the target area. Here, the reflection plane 140 is used as means for allowing the light entering in one direction to pass therethrough and the acoustic wave inputted in the other direction opposite to the one direction to be reflected, but aspects of the present invention are not limited thereto. Rather, a variety of members capable of performing such functions, including, for example, an acoustic reflection glass, can be used.

Figure 4:
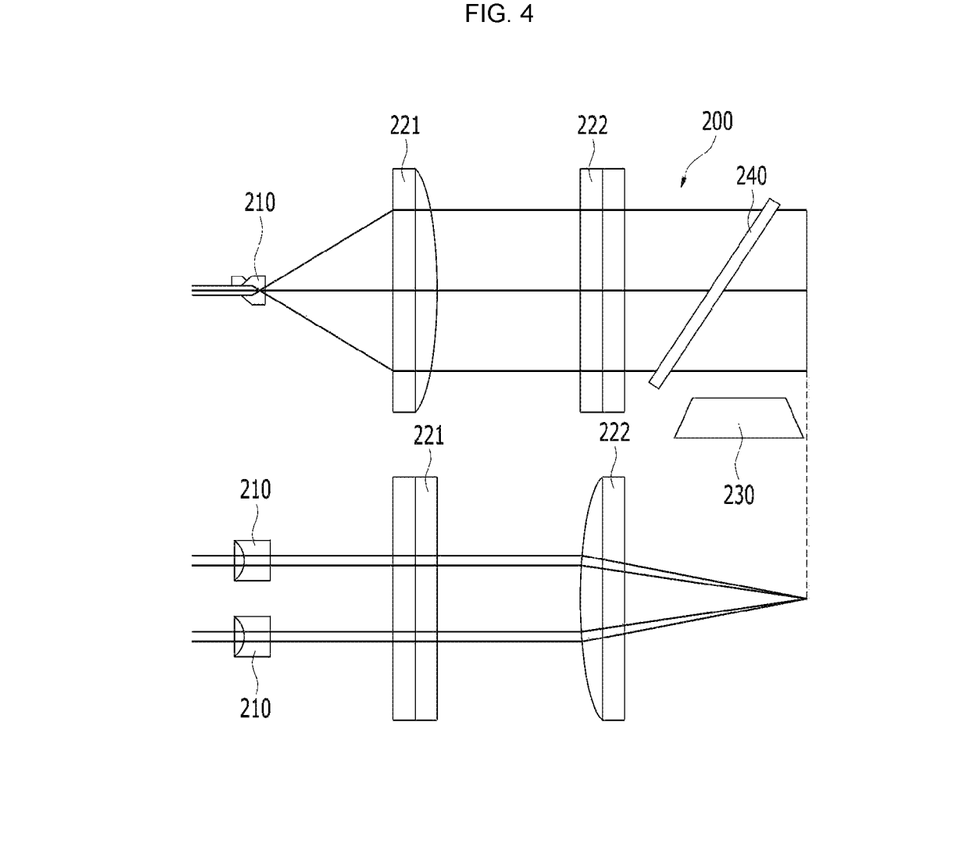
FIG. 4 is a schematic diagram illustrating an internal construction of a probe for photoacoustic tomography according to another embodiment of the present invention.

FIG. 4 illustrates a second embodiment of an internal construction of a probe 200 for photoacoustic tomography according to the present invention. In the illustrated embodiment, small diameter parallel light beams input through a pair of optical fiber input units are converted into line beams, respectively, and then line-focused on a line at a target area. Here, a plan view of an optical system is shown in the upper part of FIG. 4, and a side view of the optical system rotated at 90 degrees with respect to the plan view is shown in the lower part of FIG. 4.

Referring to FIG. 4, the photoacoustic probe 200 may include a pair of Powell lenses 210, a first cylindrical lens 221, a second cylindrical lens 222, and an acoustic measurement unit 230.

The pair of Powell lenses 210 spaced a predetermined distance apart from each other may receive parallel light beams so as to generate line beams, respectively. The first cylindrical lens 221 allows the respective line beams to pass therethrough so as to generate the respective parallel light beams having a predetermined width and a predetermined thickness in a beam traveling direction. The second cylindrical lens 222 allows the respective parallel light beams to pass therethrough so as to be line-focused at a target area as a single line beam. The acoustic measurement unit 230 may receive an acoustic wave outputted from the target area.

The pair of Powell lenses 210 may receive a pair of small diameter parallel light beams from an optical fiber through an optical fiber input unit so as to be converted into line beams, respectively. Here, each of the line beams, which has a predetermined thickness and a width increased a predetermined angle with respect to the center line of a plane, may be a beam incident to a surface perpendicular to the beam traveling direction with substantially uniform strength.

The photoacoustic probe 200 may employ an optical design using the Powell lenses, thereby irradiating light into an imaging area with uniform energy strength, thereby acquiring an image from the target area without a concentration measurement distortion of an absorptive material. Therefore, the photoacoustic probe 200 enables quantitative image acquisition, thereby accurately obtaining a precise image for the target area.

The first cylindrical lens 221 allows the respective line beams to pass therethrough so as to generate the respective parallel light beams, and the second cylindrical lens 222 allows the respective parallel light beams to pass therethrough so as to be line-focused at the target area as a single line beam. To this end, the first cylindrical lens 221 and the second cylindrical lens 222 may be arranged such that convex portions thereof are rotated at 90 degrees with respect to the central axis of the beam traveling direction while facing each other.

Here, plano-convex cylindrical lenses each configured such that a surface viewed from one side is convex may be used as the first cylindrical lens 221 and the second cylindrical lens 222, but aspects of the present invention are not limited thereto. Rather, a variety of lenses capable of performing functions of the first cylindrical lens 221 and the second cylindrical lens 222 can be employed as the first cylindrical lens 221 and the second cylindrical lens 222.

In this case, two spaced-apart optical beams meet each other through the optical system to then be line-focused on a single line, thereby enabling dark field illumination by a space between the two optical beams. During bright field illumination, as shown in FIG. 3, beams may travel along the optical axis to be irradiated into a tissue even before being focused, so that ultrasonic waves are generated thereat, acting as a noise, thereby obtaining an improved signal-to-noise ratio (SNR) can be obtained using the dark field illumination and acquiring a precise photoacoustic image for the target area.

In addition, since the respective parallel light beams are spaced apart from each other, the acoustic measurement unit 230 may be positioned in a space between the spaced-apart parallel light beams. In this case, since the acoustic measurement unit 230 is positioned in an internal space of the photoacoustic probe 200, the photoacoustic probe 200 can be advantageously miniaturized.

Here, the acoustic measurement unit 230 may be placed on a line bisecting the space between the respective parallel light beams on center lines of the parallel light beams.

Meanwhile, the second cylindrical lens 222 may convert the spaced-apart parallel light beams so as to be line-focused at the target area as a single line beam. Here, the second cylindrical lens 222 may control the focusing depth within a tissue by changing its positions while moving forward or backward along the light path. In addition, the second cylindrical lens 222 may include a variable focus lens. In this case, the focusing depth controlling structure can be easily implemented using a general focus controlling mechanism.

Here, the photoacoustic probe 200 is configured such that the focusing depth within the tissue, on which the line beam is focused, can be controlled, thereby freely controlling the focusing depth or size of the target area. Accordingly, a photoacoustic image for the target area can be easily obtained while minimizing movement of the photoacoustic probe 200.

In addition, since the focusing depth within the tissue, on which the line beam is focused, is controlled, a three-dimensional image for the target area can be obtained by performing line scanning while minimizing movement of the photoacoustic probe 200.

The acoustic measurement unit 230, which receives an acoustic wave outputted from the target area, may be the same as the acoustic measurement unit shown in the embodiment illustrated in FIG. 3. Therefore, the description of the acoustic measurement unit shown in the embodiment illustrated in FIG. 3 may be referred to in describing the acoustic measurement unit 230, and a detailed description thereof will not be given.

A reflection plane 240 may be located at a side of the target area and may allow the acoustic wave to be incident to the acoustic measurement unit 230 by allowing incident parallel light to pass therethrough and changing a traveling path of the acoustic wave outputted therefrom. In this case, the acoustic measurement unit 230 is located so as not to be interfered with the laser beam irradiated into the target area. Here, the reflection plane 240 is used as means for allowing the light entering in one direction to pass therethrough and the acoustic wave inputted in the other direction opposite to the one direction to be reflected, but aspects of the present invention are not limited thereto. Rather, a variety of members capable of performing such functions can be used.

Figure 5:
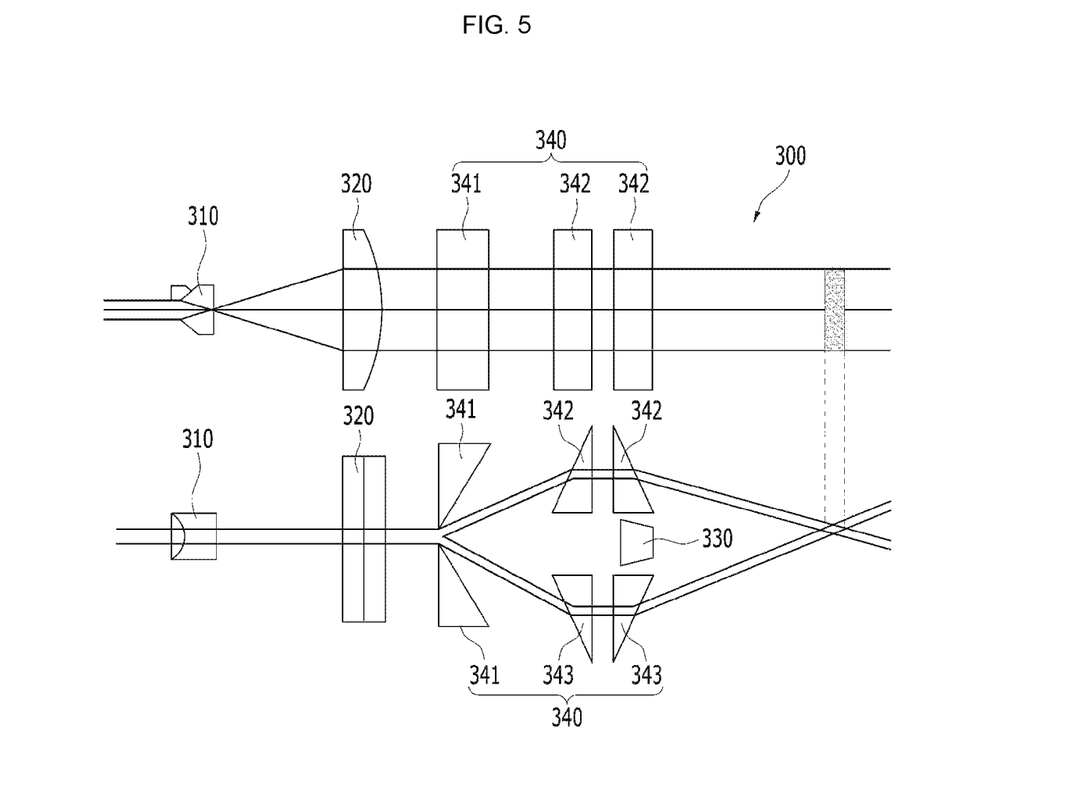
FIG. 5 is a schematic diagram illustrating an internal construction of a probe for photoacoustic tomography according to another embodiment of the present invention.

FIG. 5 illustrates a third embodiment of an internal construction of a probe 300 for photoacoustic tomography according to the present invention. In the illustrated embodiment, small diameter parallel light input from an optical fiber through an optical fiber input unit is converted into a line beam, and one parallel light is split into two parallel light beams to then be area-focused on a single area at a target area. Here, a plan view of an optical system is shown in the upper part of FIG. 5, and a side view of the optical system rotated at 90 degrees with respect to the plan view is shown in the lower part of FIG. 5.

Referring to FIG. 5, the photoacoustic probe 300 may include a Powell lens 310, a cylindrical lens 320, a light path changing unit 340, and an acoustic measurement unit 330.

The Powell lens 310 may receive a light input as small diameter parallel light so as to generate a line beam having a predetermined thickness. The cylindrical lens 320 may allow the line beam to pass therethrough so as to generate parallel light having a predetermined width and a constant thickness in a beam traveling direction. The light path changing unit 340 may allow the parallel light to pass therethrough so as to be area-focused at the target area. The acoustic measurement unit 330 may receive an acoustic wave outputted from the target area.

The Powell lens 310, which receives small diameter parallel light so as to generate a line beam, may be the same as the Powell lens shown in the embodiment illustrated in FIG. 3. Therefore, the description of the Powell lens shown in the embodiment illustrated in FIG. 3 may be referred to in describing the Powell lens 310, and a detailed description thereof will not be given.

The cylindrical lens 320 may have a convex portion positioned at a light emitting side and may allow the line beam to pass therethrough so as to generate parallel light having a predetermined width and a predetermined thickness. The cylindrical lens 320 may also have a planar portion positioned at a light emitting side.

The light path changing unit 340, which changes a light path of incident parallel light so as to be area-focused at the target area, may include a beam splitter member 341 and a pair of light path changing members 342 and 343. The beam splitter member 341 may split one parallel light beam into a first parallel light beam and a second parallel light beam. The pair of light path changing members 342 and 343 may change light paths of the first and second parallel light beams to then be area-focused at the target area, respectively.

Here, a line bessel beam can be implemented by the shown optical design, thereby increasing a depth of focus. Accordingly, area scanning can be achieved, thereby greatly increasing an image acquisition speed.

In this case, two spaced-apart optical beams (that is, the first parallel light beam and the second parallel light beam) meet each other through the optical system to then be focused on a single area, thereby enabling dark field illumination by a space between the two optical beams. Therefore, since a noise generated during bright field illumination is eliminated, an improved signal-to-noise ratio (SNR) can be obtained, thereby acquiring a precise photoacoustic image for the target area.

Here, the beam splitter member 341 may include a pair of prisms having acute angle portions adjoining each other, the acute angle portions corresponding to edges having the smallest thickness. Each of the light path changing members 342 and 343 may include a pair of prisms having right-angled faces facing each other. Here, the beam splitter member 341 and/or the light path changing members 342 and 343 are implemented as prisms, thereby easily implementing the optical system.

A structure capable of controlling the focusing depth within a tissue can be implemented by adjusting positions or angles of prisms used to change light paths of the beam splitter 341 and/or the light path changing members 342 and 343.

Here, the photoacoustic probe 300 is configured such that the focusing depth within the tissue, on which the line beam is focused, can be controlled, thereby freely controlling the focusing depth of the target area. Accordingly, a photoacoustic image for the target area can be easily obtained while minimizing movement of the photoacoustic probe 300.

In addition, since the focusing depth within the tissue, on which the line beam is focused, is controlled, a three-dimensional image for the target area can be obtained by performing area scanning while minimizing movement of the photoacoustic probe 300.

In addition, since the first and second parallel light beams are spaced apart from each other, the acoustic measurement unit 330 may be positioned in a space between the spaced-apart parallel light beams. In this case, since the acoustic measurement unit 330 is positioned in an internal space of the photoacoustic probe 300, the photoacoustic probe 300 can be advantageously miniaturized.

Here, the acoustic measurement unit 330 may be placed on a line bisecting the space between the respective parallel light beams on center lines of the parallel light beams.

Here, the acoustic measurement unit 330 may be positioned between the pair of spaced-apart light path changing members 342 and 343. In this case, the internal space of the photoacoustic probe 300 can be more efficiently utilized.

The acoustic measurement unit 330, which receives an acoustic wave outputted from the target area, may be the same as the acoustic measurement unit shown in the embodiment illustrated in FIG. 3. Therefore, the description of the acoustic measurement unit shown in the embodiment illustrated in FIG. 3 may be referred to in describing the acoustic measurement unit 330, and a detailed description thereof will not be given.

Figure 6:
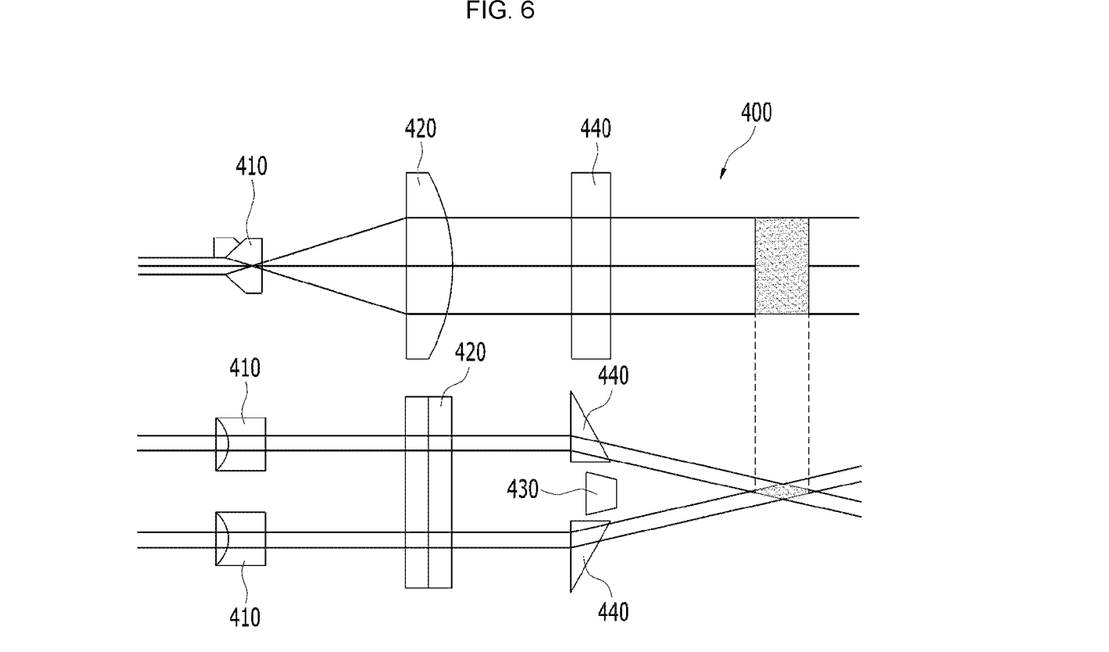
FIG. 6 is a schematic diagram illustrating an internal construction of a probe for photoacoustic tomography according to another embodiment of the present invention.

FIG. 6 illustrates a fourth embodiment of an internal construction of a probe 400 for photoacoustic tomography according to the present invention. In the illustrated embodiment, a pair of small diameter parallel light beams input from an optical fiber through an optical fiber input unit are converted into line beams to then be area-focused on a single area at a target area. Here, a plan view of an optical system is shown in the upper part of FIG. 6, and a side view of the optical system rotated at 90 degrees with respect to the plan view is shown in the lower part of FIG. 6.

Referring to FIG. 6, the photoacoustic probe 400 may include a pair of Powell lenses 410, a cylindrical lens 420, a pair of light path changing members 440, and an acoustic measurement unit 430.

The pair of Powell lenses 410 spaced a predetermined distance apart from each other may receive light inputs as parallel light beams so as to generate line beams having a predetermined thickness, respectively. The cylindrical lens 420 allows the respective line beams to pass therethrough so as to generate the respective parallel light beams having a predetermined width and a predetermined thickness in a beam traveling direction. The pair of light path changing members 440 change light paths of the respective parallel light beams so as to be area-focused at the target area. The acoustic measurement unit 430 may receive an acoustic wave outputted from the target area.

The pair of Powell lenses 410, which receive the small diameter parallel light beams to generate line beams, may be the same as the Powell lens shown in the embodiment illustrated in FIG. 4. Therefore, the description of the Powell lens shown in the embodiment illustrated in FIG. 4 may be referred to in describing the Powell lenses 410, and a detailed description thereof will not be given.

The cylindrical lens 420 may have a convex portion positioned at a light emitting side and may allow the line beams to pass therethrough so as to generate parallel light beams having a predetermined width and a predetermined thickness. The cylinder lens 420 may also have a planar portion positioned at a light emitting side. The cylindrical lens 420 allows two line beams to pass therethrough so as to generate the to be generated as parallel light beams spaced up and down a predetermined distance apart from each other.

The pair of light path changing members 440 may include a pair of prisms spaced apart from each other and having right-angled faces facing each other. Therefore, the light path changing members 440 are implemented as prisms, thereby easily implementing the an optical system.

Here, a line bessel beam can be implemented by the shown optical design, thereby increasing a depth of focus. Accordingly, area scanning can be achieved, thereby greatly increasing an image acquisition speed.

In this case, two spaced-apart optical beams meet each other through the optical system to then be focused on a single area, thereby enabling dark field illumination by a space between the two optical beams. Therefore, since a noise generated during bright field illumination is eliminated, an improved signal-to-noise ratio (SNR) can be obtained, thereby acquiring a precise photoacoustic image for the target area.

A structure capable of controlling the focusing depth within a tissue can be implemented by adjusting positions or angles of prisms used to change light paths of the light path changing members 440.

Here, the photoacoustic probe 400 is configured such that the focusing depth within the tissue, on which the line beam is focused, can be controlled, thereby freely controlling the focusing depth of the target area. Accordingly, a photoacoustic image for the target area can be easily obtained while minimizing movement of the photoacoustic probe 400.

In addition, since the focusing depth within the tissue, on which the line beam is focused, is controlled, a three-dimensional image for the target area can be obtained by performing area scanning while minimizing movement of the photoacoustic probe 400.

In addition, since the parallel light beams are spaced apart from each other, the acoustic measurement unit 430 may be positioned in a space between the spaced-apart parallel light beams. In this case, since the acoustic measurement unit 430 is positioned in an internal space of the photoacoustic probe 400, the photoacoustic probe 400 can be advantageously miniaturized.

Here, the acoustic measurement unit 430 may be placed on a line bisecting the space between the respective parallel light beams on center lines of the parallel light beams.

Here, the acoustic measurement unit 430 may be positioned between the pair of spaced-apart prisms 440. In this case, the internal space of the photoacoustic probe 400 can be more efficiently utilized.

The acoustic measurement unit 430, which receives an acoustic wave outputted from the target area, may be the same as the acoustic measurement unit shown in the embodiment illustrated in FIG. 5. Therefore, the description of the acoustic measurement unit shown in the embodiment illustrated in FIG. 5 may be referred to in describing the acoustic measurement unit 430, and a detailed description thereof will not be given.

As described above, according to the present invention, line-by-line scanning or area-by-area scanning can be performed by using a small number of light inputs, thereby quickly acquiring an image for a wide area using a simple device.

While the invention has been described in detail with particular reference to certain preferred embodiments and application examples thereof, it is not intended to be limited to the particular embodiments and application examples disclosed, but rather to cover all modifications, equivalents, and alternatives falling within the spirit and scope of this disclosure, and various modifications can be effected by a person of ordinary skill in the art within the spirit and scope of the invention. It will thus be appreciated that those modifications should not be separately understood from the technical spirit and prospect of the invention.

What is claimed is:

1. A probe for photoacoustic tomography comprising:
a Powell lens for converting a beam having a circular cross section into a line beam with uniform energy distribution;
a first cylindrical lens and a second cylindrical lens arranged sequentially in a traveling direction of the line beam from the Powell lens so that the line beam has a constant width and a reduced thickness while the line beam passes therethrough the first cylindrical lens and the second cylindrical lens, thereby focusing on a target area; and
an acoustic measurement unit for receiving an acoustic wave outputted from the target area in response to the line beam focused on the target area, wherein the second cylindrical lens is disposed to be rotated at 90 degrees relative to the first cylindrical lens with respect to the central axis of the beam traveling direction.

2. The probe of claim 1, wherein a convex surface of the first cylindrical lens and a convex surface of the second cylindrical lens face each other.

3. The probe of claim 1, wherein the Powell lens includes a pair of Powell lenses spaced a predetermined distance apart from each other, line beams generated from each of the pair of Powell lenses are irradiated to the first cylindrical lens in parallel with each other.

4. The probe of claim 1, wherein each of the first cylindrical lens and the second cylindrical lens has a flat surface on one side thereof and a convex surface on the other side thereof, the first cylindrical lens has the convex surface toward the target area.

5. The probe of claim 1, further comprising a reflector located at a side of the target area to allow the acoustic wave outputted from the target area to be incident to the acoustic measurement unit.

6. The probe of claim 1, wherein the second cylindrical lens is a variable focus lens capable of controlling a focusing depth within a tissue, on which the line beam is focused, at the target area.

* * * * *